United States Patent [19]

Uyeda et al.

[11] Patent Number: 5,286,485
[45] Date of Patent: Feb. 15, 1994

[54] PROCESS FOR CONTROLLING LEPIDOPTERAN PESTS

[75] Inventors: Kendrick A. Uyeda; Luis Foncerrada; Jewel M. Payne; Kenneth E. Narva, all of San Diego; George E. Schwab, La Jolla; Gregory A. Bradfisch, San Diego; August J. Sick, Oceanside, all of Calif.

[73] Assignee: Mycogen Corporation, San Diego, Calif.

[21] Appl. No.: 758,020

[22] Filed: Sep. 12, 1991

Related U.S. Application Data

[63] Continuation-in-part of Ser. No. 642,112, Jan. 16, 1991, and a continuation-in-part of Ser. No. 658,935, Feb. 21, 1991, abandoned.

[51] Int. Cl.$^5$ .................. A01N 63/00; C12N 1/20
[52] U.S. Cl. .................. 424/93 L; 935/252.5
[58] Field of Search .......... 424/93 L; 435/252.5; 536/27, 23.71

[56] References Cited

U.S. PATENT DOCUMENTS

| | | | |
|---|---|---|---|
| 4,448,885 | 5/1984 | Schnepf et al. | 435/252.3 |
| 4,467,036 | 8/1984 | Schnepf et al. | 424/93 L |
| 4,849,217 | 7/1989 | Soares et al. | 424/93 L |
| 4,853,331 | 8/1989 | Herrnstadt et al. | 424/93 L |
| 4,910,016 | 3/1990 | Gaertner et al. | 424/93 L |
| 4,996,155 | 2/1991 | Sick | 435/252.3 |
| 5,126,133 | 6/1992 | Payne | 424/93 L |

OTHER PUBLICATIONS

Schnepf, H. E. and Whitely, H. R. (1981) "Cloning and Expression of the *Bacillus thuringiensis* Crystal Protein gene in *E. coli*", Proc. Natl. Acad. Sci. USA 78:2893–2897.

Herrnstadt, C., G. G. Soares, E. R. Wilcox and D. L. Edwards (1986) "A New Strain of *Bacillus thuringiensis* with Activity Against Coleopteran Insects", Bio/Technology 4:305–308.

Krieg, A., A. M. Huger, G. A. Langenbruch and W. Schnetter (1983) "*Bacillus thuringiensis* var. tenebrionis: ein neuer gegenuber Laren Von Coleopteren wirksamer Pathotyp", Z. angew. Ent. 96:500–508.

*Primary Examiner*—Richard A. Schwartz
*Assistant Examiner*—Nancy T. Vogel
*Attorney, Agent, or Firm*—Saliwanchik & Saliwanchik

[57] ABSTRACT

The subject disclosure concerns *Bacillus thuringiensis* strains which can be used to control lepidopteran pests. The strains were previously known to control coleopteran pests. The discovery of lepidopteran activity was totally unexpected.

These B.t. strains can be formulated using standard lepidopteran formulation procedures. Means of administration are also standard.

The genes encoding lepidopteran-active toxins can be isolated from the B.t. isolates and used to transform other microbes for use to control lepidopteran pests.

1 Claim, No Drawings

PROCESS FOR CONTROLLING LEPIDOPTERAN PESTS

CROSS-REFERENCE TO RELATED APPLICATION

This application is a continuation-in-part application of pending U.S. application Ser. No. 07/642,112, filed on Jan. 16, 1991, and U.S. application Ser. No. 07/658,935, filed on Feb. 21, 1991, now abandoned.

BACKGROUND OF THE INVENTION

The most widely used microbial pesticides are derived from the bacterium *Bacillus thuringiensis*. This bacterial agent is used to control a wide range of leaf-eating caterpillars, beetles and mosquitos. *Bacillus thuringiensis* produces a proteinaceous paraspore or crystal which is toxic upon ingestion by a susceptible insect host. For example, *B. thuringiensis* var. *kurstaki* HD-1 produces a crystal called a delta endotoxin which is toxic to the larvae of a number of lepidopteran insects. The cloning and expression of this B.t. crystal protein gene in *Escherichia coli* has been described in the published literature (Schnepf, H. E. and Whitely, H. R. [1981] Proc. Natl. Acad. Sci. USA 78:2893–2897). U.S. Pat. No. 4,448,885 and U.S. Pat. No. 4,467,036 both disclose the expression of B.t. crystal protein in *E. coli*. U.S. Pat. No. 4,853,331 discloses *B. thuringiensis* strain *san diego* (B.t. sd.) which can be used to control coleopteran pests in various environments. U.S. Pat. No. 4,849,217 discloses *Bacillus thuringiensis* isolates active against the alfalfa weevil. One of the isolates disclosed is *B. thuringiensis* PS86A1 (NRRL B-18400).

BRIEF SUMMARY OF THE INVENTION

Disclosed and claimed is a novel process for controlling lepidopteran pests. This process results from the unexpected discovery that certain coleopteran-active B.t. isolates also have activity against lepidopteran pests, e.g., the diamondback moth (*Plutella xylostella*). Two known coleopteran isolates, *Bacillus thuringiensis* var. *san diego* (Herrnstadt, C., Soares, G. G., Wilcox, E. R. and Edwards, D. L. 1986. A new strain of *Bacillus thuringiensis* with activity against coleopteran insects. Bio/Technology 4:305–308) and *Bacillus thuringiensis* var. *tenebrionis* (Krieg, A. Huger, A. M., Langenbruch, G. A., Schnetter, W. 1983. *Bacillus thuringiensis* var. *tenebrionis*: ein neuer gegenuber Laren von Coleopteren wirksamer Pathotyp. Z. angew. Ent. 96: 500–508). are not toxic to lepidoptera.

More specifically, the subject invention process uses B.t. microbes, or mutants thereof, and/or their toxins, to control lepidopteran pests. The B.t. microbes of the invention are B.t. PS86A1, B.t. PS50C, and B.t. PS43F.

The subject invention also includes the genes from the B.t. isolates of the invention which genes encode the novel lepidopteran-active toxins.

Further, the subject invention also includes mutants of the B.t. isolates of the invention which have substantially the same lepidopteran-active properties as the parent B.t. isolate. Procedures for making mutants are well known in the microbiological art. Ultraviolet light and nitrosoguanidine are used extensively toward this end.

Still further, the invention also includes the treatment of substantially intact B.t. cells, and recombinant cells containing the genes of the invention, to prolong the lepidopteran activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

DETAILED DISCLOSURE OF THE INVENTION

The *Bacillus thuringiensis* isolates of the subject invention have the following characteristics in their biologically pure form:

Characteristics of B.t. PS50C

Colony morphology—Large colony, dull surface, typical B.t.

Vegetative cell morphology—typical B.t.

Culture methods—typical for B.t.

Flagellar serotyping—PS50C belongs to serotype 18, kumamotoensis.

Crystal morphology—a sphere.

RFLP analysis—Southern hybridization of total DNA distinguishes B.t. PS50C from B.t.sd. and other B.t. isolates.

Alkali-soluble proteins—SDS polyacrylamide gel electrophoresis (SDS-PAGE) shows a 130 kDa doublet protein.

A comparison of the characteristics of *B. thuringiensis* PS50C (B.t. PS50C) to the characteristics of the known B.t. strains *B. thuringiensis* var. *san diego* (B.t.sd.), *B. thuringiensis* PS86B1 (NRRL B-18299), and *B. thuringiensis* var. *kurstaki* (HD-1) is shown in Table 1.

TABLE 1

Comparison of B.t. PS50C, B.t. PS86B1, B.t.sd., and B.t. HD-1

| | B.t. PS50C | B.t.sd. | B.t. PS86B1 | B.t. HD-1 |
|---|---|---|---|---|
| Serovar | kumamotoensis | morrisoni | tolworthi | kurstaki |
| Type of inclusion | sphere | square wafer | flat, pointed ellipse, plus sm. inclusions | Bipyramid |
| Size of alkali-soluble proteins by SDS-PAGE | 130 kDa doublet | 72,000 64,000 | 75,000 68,000 61,000 | 130,000 68,000 |
| Host range | Coleoptera | Coleoptera | Coleoptera | Lepidoptera |

The characteristics of B.t. PS86A1 are as follows:

Inclusion—sphere ovoid, 3/cell.

Major protein—50 kDa

Other characteristics, e.g., colony morphology, vegetative cell morphology and culture methods are as given above for B.t. PS50C.

B.t. PS43F is disclosed in U.S. Pat. No. 4,996,155.

The subject invention process comprises the use of at least one of the B.t. isolates, listed below, or mixtures thereof, to control lepidopteran pests. The B.t. isolates of the invention are as follows:

| Culture | Accession Number | Deposit Date |
|---|---|---|
| B.t. PS86A1 | NRRL B-18400 | August 16, 1988 |
| B.t. PS50C | NRRL B-18746 | January 9, 1991 |

| Culture | Accession Number | Deposit Date |
| --- | --- | --- |
| B.t. PS43F | NRRL B-18298 | February 2, 1988 |

The cultures are on deposit in the permanent collection of the Northern Research Laboratory, U.S. Department of Agriculture, Peoria, Ill., USA.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The lepidopteran toxin genes of the subject invention can be isolated by known procedures and can be be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would being. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR323, pACYC184, RSF1010, pRO1614, and the like. See for example, Olsen et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and-positive, include Enterobacteriaceae; such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the B.t. lepidopteran toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. lepidopteran gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *Bacillus thuringiensis* Isolates

A subculture of a B.t. isolate of the invention can be used to inoculate the following medium, a peptone, glucose, salts medium.

| Bacto Peptone | 7.50 g/l |
|---|---|
| Glucose | 1.00 g/l |
| $KH_2PO_4$ | 3.40 g/l |
| $K_2HPO_4$ | 4.35 g/l |
| Salt Solution | 5.00 ml/l |
| $CaCl_2$ Solution | 5.00 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Testing of B.t. Isolates against the Diamondback Moth (A) A spore crystal preparation of a B.t. clone comprising the PS86A1 gene was toxic to the lepidopteran pest, diamondback moth *Plutella xylostella* in a 1% agar artificial diet assay. The B.t. clone was grown as disclosed in Example 1. Rates greater than 100 microgram protein/gram diet gave 100% control of this pest in 6 days.

(B) A spore crystal preparation of a B.t. clone comprising the PS50C gene was toxic to the lepidopteran pest, diamondback moth in a 1.5% agar artificial diet assay. The B.t. clone was grown as disclosed in Example 1. Rates greater than 100 mircogram protein/gram diet gave 100% control of this pest in 6 days.

(C) A *Pseudomonas fluorescens* clone comprising the PS43F gene was toxic to the lepidopteran pest, diamondback moth, in a 1.5% agar artificial diet assay. Rates greater than 40 microgram protein/gram diet gave 100% control of this pest in 6 days.

EXAMPLE 3

Insertion of Toxin Genes Into Plants

The novel genes, obtainable from the B.t. isolates of the invention, coding for novel lepidopteran-active toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J. [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *Bacillus thuringiensis* Genes Into Baculoviruses

The novel genes, obtainable from the B.t. isolates disclosed herein, can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The gene(s) coding for the novel protein(s) toxin can be modified with BamHI linkers at appropriate regions both upstream and downstream from the coding region and inserted into the passenger site of one of the AcNPV vectors.

We claim:

1. A process for controlling lepidopteran insect pests which comprises contacting said insect pests with an insect-controlling effective amount of, *Bacillus thuringiensis* isolate PS50C, or mutants thereof.

* * * * *

UNITED STATES PATENT AND TRADEMARK OFFICE
CERTIFICATE OF CORRECTION

PATENT NO. : 5,286,485
DATED : February 15, 1994
INVENTOR(S) : Uyeda, et. al.

It is certified that error appears in the above-indentified patent and that said Letters Patent is hereby corrected as shown below:

Column 4  line 48: Delete "would being." and insert --would begin.--

Column 5  line 68: Delete "pBR323" and insert --pBR322--.

Column 8  line 65: Delete "mircogram" and insert --microgram--.

Signed and Sealed this

Nineteenth Day of July, 1994

Attest:

BRUCE LEHMAN

*Attesting Officer*          *Commissioner of Patents and Trademarks*